(12) United States Patent
Green et al.

(10) Patent No.: US 7,551,954 B2
(45) Date of Patent: *Jun. 23, 2009

(54) MAGNETIC RESONANCE IMAGING WITH ADJUSTABLE FIXTURE APPARATUS

(75) Inventors: Charles A. Green, Holbrook, NY (US); William H. Wahl, Smithtown, NY (US); Arto Cinoglu, Mellville, NY (US)

(73) Assignee: Fonar Corporation, Melville, NY (US)

( * ) Notice: Subject to any disclaimer, the term of this patent is extended or adjusted under 35 U.S.C. 154(b) by 428 days.

This patent is subject to a terminal disclaimer.

(21) Appl. No.: 10/131,843

(22) Filed: Apr. 25, 2002

(65) Prior Publication Data

US 2003/0204136 A1 Oct. 30, 2003

(51) Int. Cl.
*A61B 5/05* (2006.01)
*A47B 23/00* (2006.01)
(52) U.S. Cl. .......................................... 600/415; 5/617
(58) Field of Classification Search ................ 600/410, 600/411, 415; 5/601, 610, 611, 18.1, 617, 5/621–624, 632, 635
See application file for complete search history.

(56) References Cited

U.S. PATENT DOCUMENTS

| | | | |
|---|---|---|---|
| 4,629,989 A | 12/1986 | Riehl et al. | |
| 4,891,596 A | 1/1990 | Mitomi et al. | |
| 4,943,775 A * | 7/1990 | Boskamp et al. | 324/322 |
| 4,968,937 A | 11/1990 | Akgun | |
| 4,985,678 A | 1/1991 | Gangarosa et al. | |
| 5,008,624 A | 4/1991 | Yoshida | |
| 5,065,761 A | 11/1991 | Pell | |
| 5,085,219 A * | 2/1992 | Ortendahl et al. | 600/422 |
| 5,197,474 A | 3/1993 | Englund et al. | |
| 5,221,902 A | 6/1993 | Jones et al. | |
| 5,274,332 A | 12/1993 | Jaskolski et al. | |
| 5,307,806 A | 5/1994 | Jones | |
| 5,349,956 A | 9/1994 | Bonutti | |
| 5,473,251 A | 12/1995 | Mori | |
| 5,519,321 A | 5/1996 | Hagen et al. | |
| 5,520,181 A | 5/1996 | Kreidler et al. | |
| 5,640,958 A | 6/1997 | Bonutti | |
| 5,680,861 A * | 10/1997 | Rohling | 600/407 |
| 5,735,278 A | 4/1998 | Hoult et al. | |
| 5,743,264 A * | 4/1998 | Bonutti | 600/415 |
| 5,762,073 A * | 6/1998 | Choy | 128/846 |
| 5,779,637 A * | 7/1998 | Palkovich et al. | 600/415 |
| 5,926,876 A * | 7/1999 | Haigh et al. | 5/617 |

(Continued)

FOREIGN PATENT DOCUMENTS

JP 1305937 12/1989

(Continued)

*Primary Examiner*—Brian Casler
*Assistant Examiner*—Parikha S Mehta
(74) *Attorney, Agent, or Firm*—Lerner, David, Littenberg, Krumholz & Mentlik, LLP

(57) ABSTRACT

A fixture such as a local receiver coil is secured to the patient support of a magnetic resonance imaging system so that the fixture remains in position relative to the support even when the support is in a vertical orientation. The positioning apparatus is arranged to allow adjustment of the fixture position, but to limit such adjustment so that the fixture cannot interfere with the poles or other elements defining the patient-receiving gap of the magnet during movement of the patient support.

23 Claims, 10 Drawing Sheets

U.S. PATENT DOCUMENTS

| | | | |
|---|---|---|---|
| 6,037,773 A * | 3/2000 | Mitsumata et al. | 324/318 |
| 6,141,579 A | 10/2000 | Bonutti | |
| 6,278,274 B1 * | 8/2001 | Biglieri et al. | 324/318 |
| 6,385,481 B2 * | 5/2002 | Nose et al. | 600/415 |
| 6,414,490 B1 | 7/2002 | Damadian et al. | |
| 7,006,860 B2 | 2/2006 | Menon | |
| 2001/0007054 A1 | 7/2001 | Furuta et al. | |

FOREIGN PATENT DOCUMENTS

| | | |
|---|---|---|
| JP | 928690 | 2/1997 |
| JP | 10-57335 | 3/1998 |
| JP | 10113540 | 5/1998 |

\* cited by examiner

MAGNETIC RESONANCE IMAGING WITH ADJUSTABLE FIXTURE APPARATUS

FIELD OF INVENTION

The present invention relates to the art of magnetic resonance imaging.

BACKGROUND OF THE INVENTION

In magnetic resonance imaging ("MRI"), the body of a subject to be imaged as, for example, the body of a medical patient, is subjected to a strong static magnetic field. Radio frequency ("RF") excitation signals are applied to the subject. This causes the tissues of the subject's body to emit minuscule radio frequency signals referred to herein as "magnetic resonance signals." During the procedure, magnetic field gradients are applied so that, during different portions of the procedure, the strength of the static magnetic field varies with distance along various axes. The resulting magnetic resonance signals are spatially encoded. Thus, the magnetic resonance signals typically are generated only in a limited region as, for example, a single point, a line or a two dimensional "slice." Moreover, the signals from different portions of a line or a slice differ in frequency or phase from one another. If the procedure is repeated numerous times, it is possible, using known techniques, to recover an image data set having data elements, each representing one or more properties of the magnetic resonance signals generated within a single, small volume element or "voxel." Because properties of magnetic resonance signals vary with the composition of the material generating the signal, the signals generated by different tissues within the body will differ from one another. Thus, data elements representing voxels in different tissues will have different values. Such a data set can be used, for example, to provide a visually perceptible image such as a screen display or a printed picture showing different tissues within the body with different brightness or color.

Magnetic resonance imaging offers numerous advantages over other imaging techniques such as conventional x-ray imaging, fluoroscopy and CAT x-ray scanning. For example, MRI is capable of showing soft tissues in extraordinary detail and is capable of displaying subtle anatomical differences. Moreover, MRI does not require exposure of the subject or medical personnel to ionizing radiation.

Many conventional magnetic resonance imaging instruments require that a patient lie on a horizontal bed that is then advanced into a tubular bore within a superconducting solenoidal magnet used to generate the static magnetic field. Other conventional MRI imaging instruments use a magnet having a ferromagnetic frame defining a patient-receiving space. Considerable effort has been devoted to design of such magnets in a manner which provides a relatively open patient-receiving space, as opposed to the claustrophobic tubular bore of the conventional solenoidal magnet. However, in these instruments as well, it has been the common practice to provide the patient on a bed which remains horizontal throughout the procedure.

It is often desirable to provide fixtures in close proximity to the patient. For example, local antennas such as small solenoidal coils can be placed around a part of the patient's body to be imaged as, for example, around the head or around a limb of the patient. These antennas can be used to transmit the RF excitation signals, to receive the magnetic resonance signals emitted by the tissue, or both. Such local antennas allow improved reception of signals from the specific region of interest within the patient's body. Other fixtures can be used for purposes such as supporting or positioning parts of the patient's body relative to the table as, for example, a rest for supporting the patient's head or limb. Typically, these fixtures are simply placed on the surface of the bed at the desired location for a particular patient, or are placed on the patient's body so that the fixture will be supported by the bed surface when the patient lies on the bed surface. These arrangements are satisfactory where the bed remains in a horizontal position at all times.

As described in greater detail in copending, commonly assigned U.S. patent application Ser. Nos. 08/978,084 and 09/718,946, the disclosures of which are hereby incorporated by reference herein, a magnetic resonance imaging system can be provided with a patient support such as a table which can extend in a generally vertical direction so that the long axis of the patient is substantially vertical. For example, the patient may be in a standing posture, with his back, side or front leaning against a generally vertical patient support. Such a support may include a footrest projecting from the table at its lower end and the patient may stand on the footrest. In other arrangements, the support includes a seat projecting from the table so that the seat is in a horizontal plane when the table surface is vertical. In particularly preferred arrangements, the patient support can move relative to the magnet. For example, the patient support may be arranged to move vertically relative to the magnet so as to elevate a portion of the patient into the patient-receiving space of the magnet. Alternatively or additionally, the patient support may be arranged to tilt through a range of orientations between a generally horizontal orientation and a generally vertical orientation.

Where the patient support table is in a generally vertical orientation during all or a portion of the procedure, fixtures positioned on the surface of the support will fall off of the support unless they are secured to the surface. Although the fixtures can be secured to the support using devices improvised for a particular application, as, for example, straps or tape, such arrangements do not offer a complete solution. Accordingly, there has been a need for improved apparatus for positioning fixtures in magnetic resonance apparatus, and for magnetic resonance apparatus incorporating such improved positioning apparatus.

SUMMARY OF THE INVENTION

One aspect of the present invention provides a magnetic resonance imaging system which includes magnetic resonance apparatus having a structure including elements defining a patient-receiving gap and also including a patient support moveable relative to the structure through a range of support positions. The imaging system according to this aspect of the invention desirably includes a fixture positioning apparatus and a fixture. The fixture positioning apparatus is operative to secure the fixture to the patient support and to permit adjustment of the fixture relative to the patient support over a range of fixture positions. Most preferably, the range of fixture positions allowed by the fixture positioning apparatus is limited so that for any position of the fixture within the range of fixture positions, the fixture will remain clear of the elements of the structure defining the gap during movement of the patient support. A system according to this aspect of the invention provides adjustability of the fixture as required to meet patient needs, but also provides significant safety benefits. The fixture positioning apparatus prevents the technician from accidentally setting the position of the fixture relative to the support in such a manner that movement of the support will cause the fixture to crash into the gap-defining structure of the magnet.

Typically, the support has a longitudinal direction. The support may be positioned or positionable in an orientation such that the longitudinal direction of the support extends generally vertically. The range of support positions may include a range of movement in the longitudinal direction of the support. The support typically has a pair of longitudinal edges extending in the longitudinal direction. The range of fixture positions afforded by the fixture positioning apparatus most preferably includes a range of positions in a lateral direction transverse to the longitudinal direction. Desirably, the range of positions in the lateral direction is limited so that, for any position of the fixture within this range of positions in the lateral direction, the fixture is disposed entirely between the longitudinal edges of the patient support.

Preferably, the fixture positioning apparatus includes a mounting unit and one or more mount attachments which connect the mounting unit to the patient table, as well as a fixture-receiving unit adapted to engage the fixture. The fixture-receiving unit is adjustable relative to the mounting unit and preferably is adjustable relative to the mounting unit in the lateral direction, so as to provide the adjustability discussed above. In a particularly preferred arrangement, the patient support of the magnetic resonance imaging system includes one or more support tracks extending in the longitudinal direction of the support and the mount attachments include one or more guide elements arranged to engage the support tracks so that the mounting unit can be adjusted relative to the patient support in the longitudinal direction. The mount attachments desirably also include one or more arresting elements engaged with the mounting unit and with the patient support, so as to arrest the movement of the mounting unit relative to the patient support. Most preferably, the fixture-receiving unit includes a releasable connection which releasably holds the fixture to the fixture-receiving unit, so that the fixture can be removed. One or more additional fixtures can be provided, and the releasable connection of the fixture-receiving unit is arranged to engage any of the fixtures. Thus, the fixtures are interchangeable. The additional fixtures may be of different configurations to meet different patient needs.

A further aspect of the invention provides fixture-positioning apparatus for use in a magnetic resonance imaging system as discussed above. The fixture-positioning apparatus according to this aspect of the invention desirably includes a mounting unit and one or more mount attachments adapted to connect the mounting unit to a patient support of a magnetic resonance apparatus. The fixture-positioning apparatus further includes a fixture-receiving unit adapted to hold a fixture. The fixture-receiving unit and the mounting unit desirably are engagable with one another, so that the fixture-receiving unit can be adjusted over a range of positions relative to the mounting unit. This allows adjustment of the fixture held in the fixture-receiving unit relative to the patient support, as discussed above. The mounting unit desirably defines a track direction, and the mount attachments are arranged to secure the mounting unit to the patient support, so that the track direction is transverse to the direction of elongation of the support. The fixture-receiving unit desirably is slideable in the track direction relative to the mounting unit when the fixture-receiving unit is engaged with the mounting unit.

The fixture-receiving unit and mounting unit desirably have stops engagable with one another, so as to limit the position of the fixture-receiving unit in the track direction. The fixture-receiving unit may be adapted to hold a fixture in the form of a coil so that the axis of the coil extends transverse to the track direction and, hence, extends in the longitudinal direction of the patient support when the unit is assembled with the patient support. Preferably, the fixture-receiving unit defines a cradle having an axis disposed transverse to the track direction and also includes one or more releasable latches arranged to engage corresponding features on coils or other fixtures. In a particularly preferred arrangement, detents are provided for holding the fixture-receiving unit at predetermined locations within its range of motion in the track direction.

The preferred positioning apparatus and magnetic resonance systems in accordance with these aspects of the present invention provide secure attachment of fixtures to the patient support and are operable with the support in a vertical orientation, as well as other orientations such as a horizontal orientation, a Trendelenburg orientation in which the head end of the fixture, with the patient's head is lower than the foot end, and intermediate orientations. The most preferred structures in accordance with these aspects of the invention provide the versatility needed to accommodate a wide range of procedures using various fixtures disposed in various locations, and also provide for quick changes of fixtures and positions. Moreover, the preferred apparatus and systems according to these aspects of the invention provide significant safety benefits.

A further aspect of the invention provides methods of operating a magnetic resonance system. A method according to this aspect of the invention desirably includes the steps of positioning a first fixture on a patient support of a magnetic resonance apparatus using a fixture positioning apparatus and adjusting the position of the fixture relative to the patient support by adjusting the fixture positioning apparatus. Preferably, the method also includes the step of moving the patient support within a range of support positions between a pair of magnet elements defining a gap. Most desirably, the fixture positioning apparatus limiting the position of the fixture after completion of the adjusting step so that the fixture does not interfere with the pair of magnet elements during the step of moving the patient support. Methods according to this aspect of the invention may include the further step of disengaging the fixture from the fixture positioning apparatus and replacing the fixture with another fixture. The adjusting and moving steps can be repeated using the new fixture.

DETAILED DESCRIPTION OF THE PREFERRED EMBODIMENTS

Figure 1:
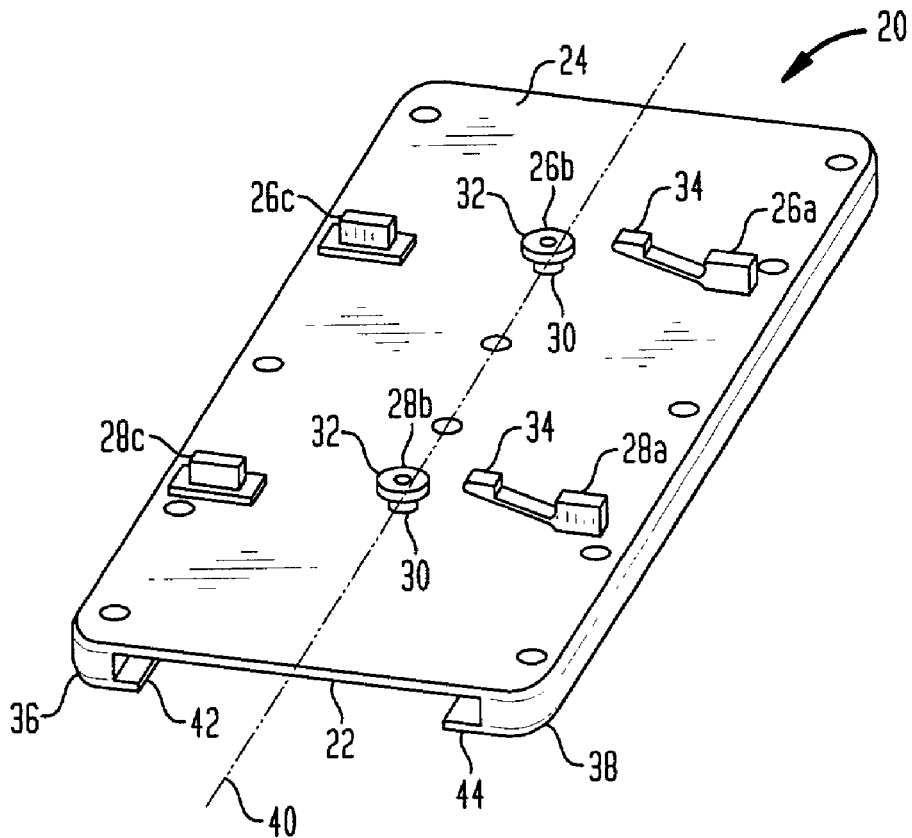
FIG. 1 is a diagrammatic perspective view of a component of a fixture-positioning apparatus according to one embodiment of the invention.
Figure 2:
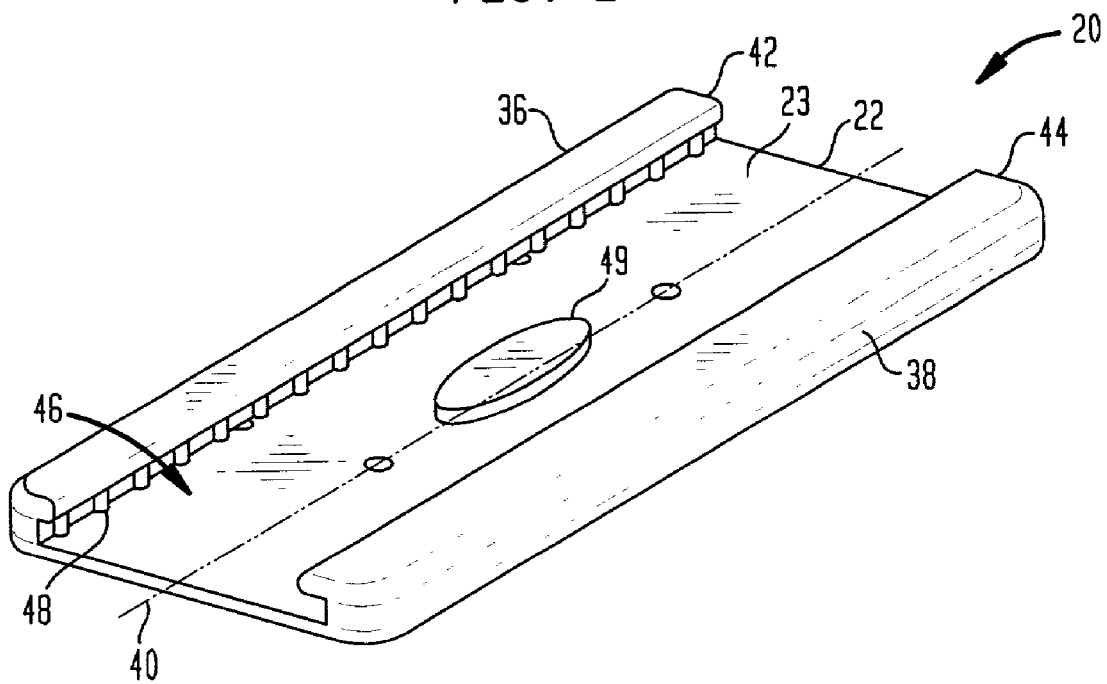
FIG. 2 is a perspective view, from an opposite perspective, of the components shown in FIG. 1.

A positioning apparatus in accordance with one embodiment of the invention includes a mounting unit 20 (FIGS. 1 and 2). The mounting unit includes a lower plate 22 having a bottom surface 24. A first set of guide elements 26*a*-26*c* projects from the bottom face in a row extending across the bottom plate. A second set of guide elements 28*a*-28*c* also projects from the bottom face. The guide elements of the second set are arranged in a row parallel to the row formed by the first set of guide elements 26. The first set of guide elements includes a center guide element 26*b* in the form of a shoulder bolt having a relatively small diameter neck portion 30 adjacent the bottom face 24 of the bottom plate and having a relatively large diameter head 32 spaced away from the bottom face 24. The remaining guide units 26*a* and 26*c* of the first set are generally rectangular, solid elements. The guide elements 28 of the second set include end elements 28*a* and 28*c*, similar to the end elements 26*a* and 26*c* of the first set, and a center guide element 28*b*, similar to those of center guide element 26*b*. A pair of resilient arresting elements 34 is formed integrally with the end guide elements 26*a* and 28*a*. These end elements are flexible in directions towards and away from the bottom plate 22, i.e., upwardly and downwardly as seen in FIG. 1.

As depicted in FIG. 2, mounting unit 20 is inverted relative to the position shown in FIG. 1, so that the top surface 23 of the bottom plate 22 is facing upwardly in FIG. 2. The mounting unit has a pair of side rails 36 and 38 projecting upwardly from the top surface 23. The side rails extend generally in a track direction, i.e., the direction indicated by axis 40. Rails 36 and 38 (FIG. 2) extend generally along opposite edges of bottom plate 22. The first rail 36 has a flange 42 projecting inwardly from the upper end of the rail, i.e., the edge of the rail remote from bottom plate 22. The second rail 38 has a similar flange 44 projecting inwardly towards rail 36. The rails, flanges and bottom plate 22 cooperatively define a track in the form of a generally T-shaped slot 46 extending in track direction 40. The first rail 36 is provided with a series of detent bumps 48 disposed between flange 42 and bottom plate 22. Detent bumps 48 are disposed at regular intervals as, for example, about 2.5 cm (one inch) between detent bumps. A stop 49 projects upwardly from the top surface 23 of bottom plate 22 within slot 46. As seen in FIG. 1, the first rows of guide elements extend transverse to the track direction 40 and the second row of guide elements 28 also extends transverse to the track direction.

A fixture-receiving unit 50 (FIGS. 3 and 4) includes a base plate 52 having a pair of oppositely directed long edges 54 and 56 and an elongated central slot 58. A pair of end risers 60 and 62 project upwardly from the base plate 52 at opposite ends thereof. End riser 62 has a generally rectangular slot 64 in its inner face, the face of riser 62 facing toward the opposite riser 60. Slot 64 is open to the upper end of riser 62 facing away from base plate 52.

A latch 66 projects into slot 64. The latch has a gradually sloping face facing toward the open end of slot 64. Latch 66 is carried on a resilient spring arm 68, seen in broken lines in FIG. 3, disposed within a cavity in end unit 64. The cavity is covered by a plate 70. A release button 72 is exposed at an edge of end unit 62. Button 72 is connected through a rod 74 to spring arm 68, so that when button 72 is depressed manually, latch 66 is moved out of slot 64. The opposite end unit 60 has a slot 76 equipped with a similar latch 77, resilient arm 79, and a similar release button 78.

A pair of plates 80 and 82 projects upwardly from the base plate 52 and extend between end risers 60 and 62. Plates 80 and 82 are spaced inwardly from edges 54 and 56 of the base plate 52. Thus, a region of the base plate between first edge 54 and plate 80 defines a first lip 84, whereas another portion of the base plate between plate 82 and second edge 56 defines another lip 86. Plates 80 and 82 have semicircular indentations 88 and 90 in their top edges so that these plates cooperatively define a cradle in the form of a sector of a circular cylinder having a cradle axis 92. The cradle axis extends transverse to the edges 54 and 56 of the base plate and, hence, transverse to the direction of elongation of the base plate.

Figure 4:
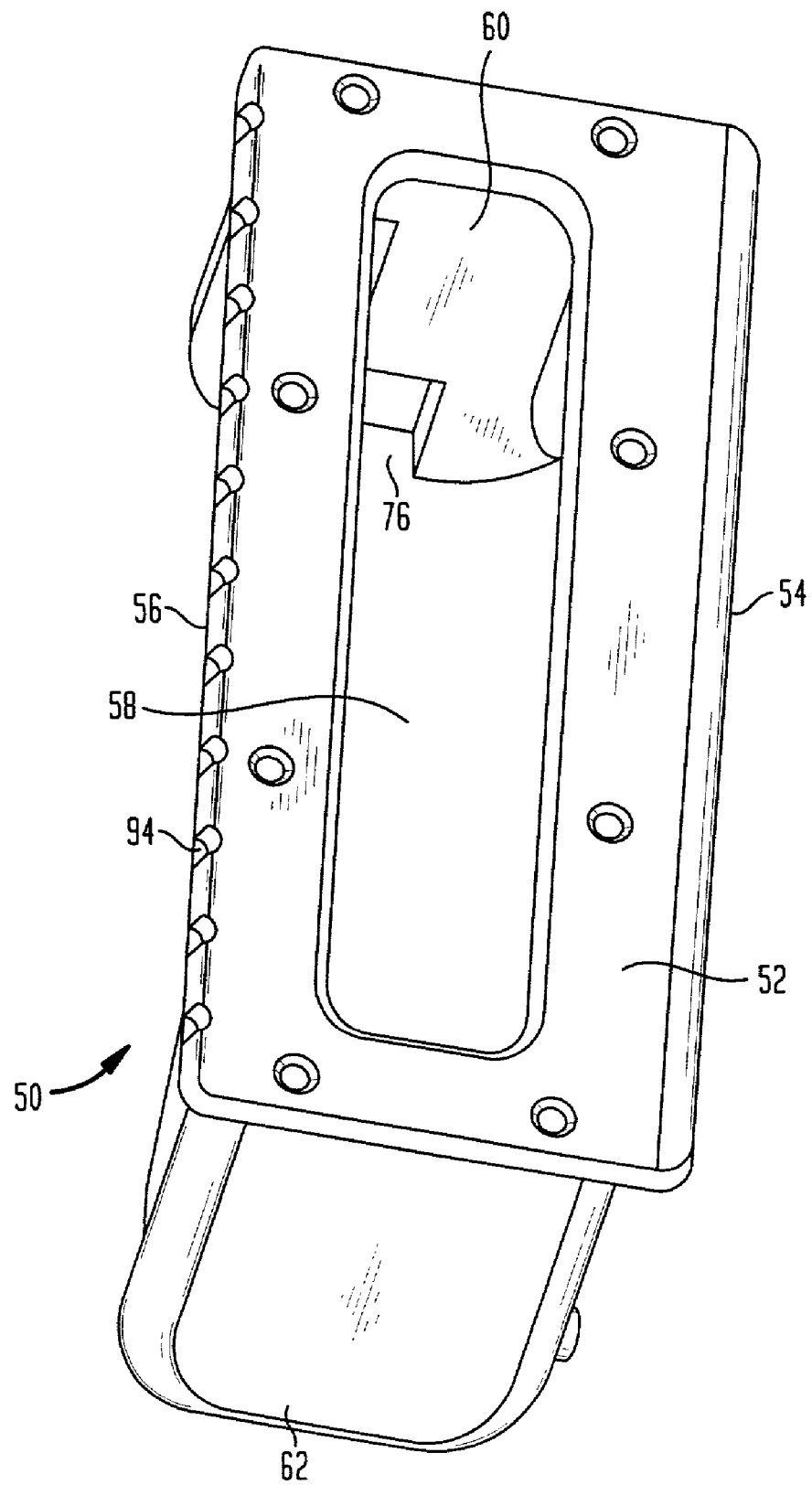
FIG. 4 is a diagrammatic perspective view, from an opposite perspective, of the component shown in FIG. 3.

As best seen in FIG. 4, the second edge 56 of base plate 54 is provided with a series of detent notches 94 spaced apart from one another at regular intervals along the length of the edge. The spacings between notches 94 correspond to the spacings between detent bumps 48 of the mounting unit (FIG. 2).

Figure 5:
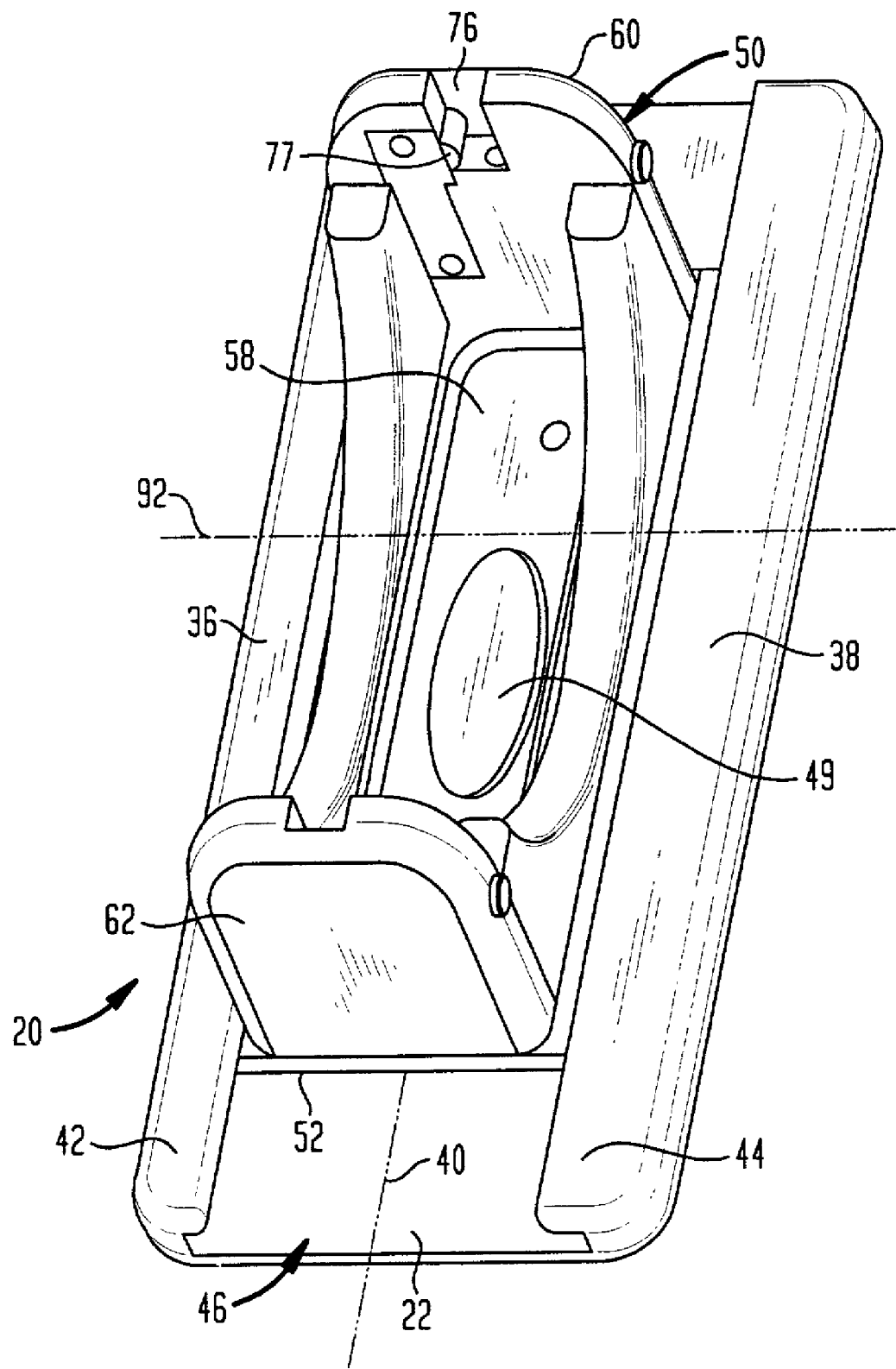
FIG. 5 is a diagrammatic perspective view of the fixture-positioning apparatus incorporating the components of FIGS. 1-4.

As seen in FIG. 5, fixture-receiving unit 50 is assembled with mounting unit 20 so that the base plate 52 of the fixture-receiving unit is disposed in the slot 46 of the mounting unit. Thus, the lips at the edges of the base plate are disposed beneath the flanges 42 and 44 of the mounting unit. The lengthwise direction of base plate 52 and, hence, edges 54 and 56 (FIGS. 3 and 4) extend in the track direction 40 defined by the mounting unit. The cradle axis 92 of the fixture-receiving unit is perpendicular to the track direction 40. The second edge 56 (FIG. 4) of the base plate on the fixture-receiving unit is disposed beneath flange 42 of the first rail 36 on the mounting unit, whereas the first edge 54 of the fixture-receiving unit (FIG. 4) is disposed beneath flange 42 of the second rail 38. In the position illustrated in FIG. 5, some of the detent notches 94 (FIG. 4) on the base plate 52 are engaged with some of the detent bumps 48 (FIG. 2) on first rail 36. However, the distance between edges 56 and 54 of the fixture-receiving base plate is slightly less than the distance between rails 36 and 38, so that the fixture-receiving unit can be shifted slightly in the direction towards rail 38 and transverse to track direction 40 to disengage the detent bumps and detent notches. In this shifted condition, the fixture-receiving unit 50 is slideable along track or slot 46 in track direction 40 relative to the mounting unit 20.

Stop 49 of the mounting unit is disposed within slot 58 of the base plate. The stop limits the range of travel of the fixture-receiving unit relative to the mounting unit. At one extreme, the first end riser 60 of the fixture-receiving unit is aligned with the end of mounting unit 20 towards the top of the drawing in FIG. 5. At the opposite extreme of the range of motion, the other end riser 62 is aligned with the opposite end of mounting unit 20. Thus, at all positions within the range of motion allowed by stop 49 and slot 58, the fixture-receiving unit 50 is disposed entirely within the length of mounting unit 20 in the track direction 20.

Figure 6:
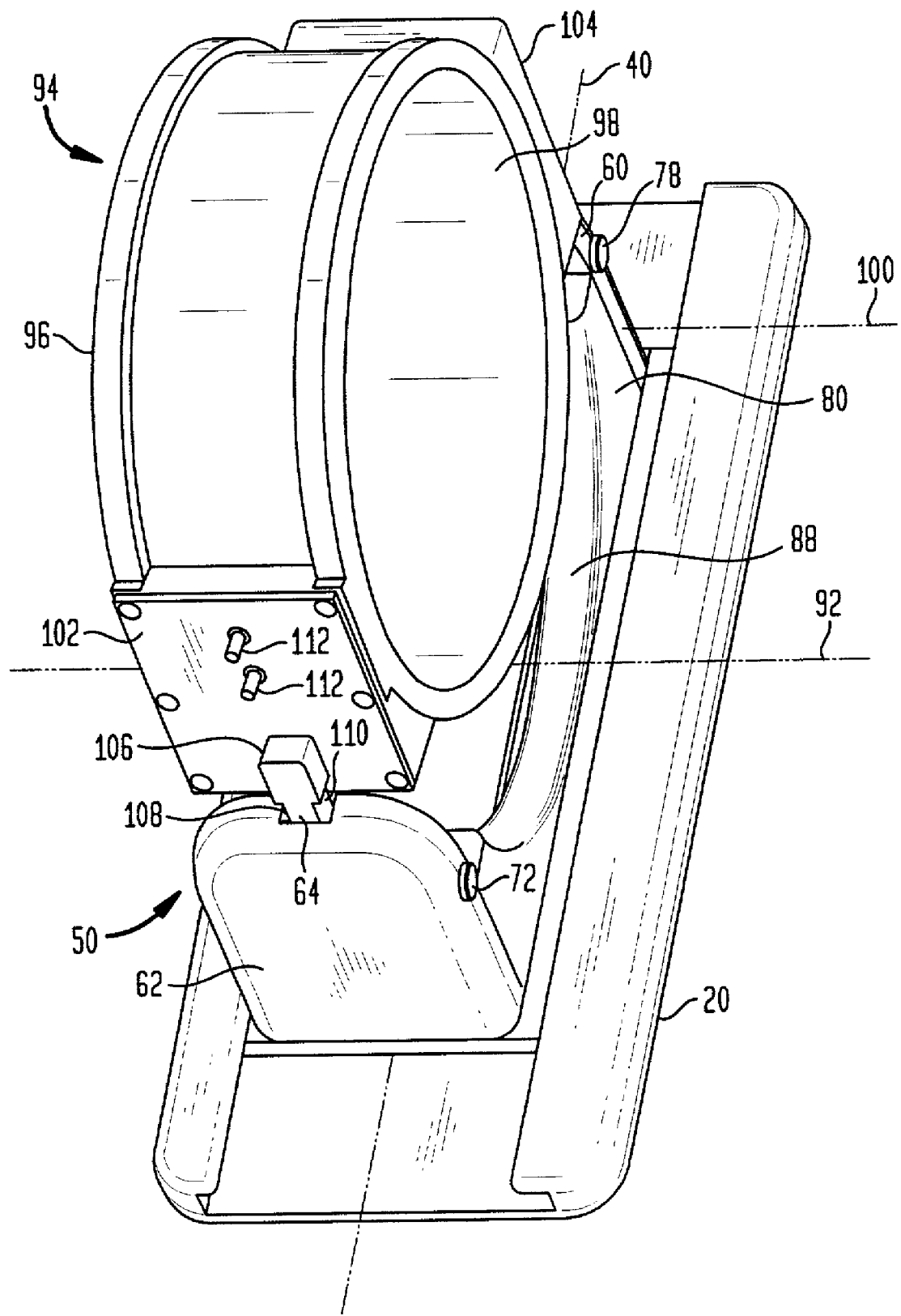
FIG. 6 is a diagrammatic perspective view of the apparatus shown in FIG. 5 in conjunction with a fixture.

As shown in FIG. 6, the fixture-positioning assembly of FIGS. 1-5 can be used with a fixture such as a local RF coil 94. The coil includes generally conventional windings enclosed in a toroidal housing 96 having an interior bore 98. The coil defines a coil axis 100 extending through the center of the bore. Coil 94 also has a pair of mounting pads 102 and 104. Pad 102 defines a flat surface having a generally rectangular block 106 projecting from such surface. Block 106 has notches 108 and 110 extending into it from opposite sides. Block 106 is elongated in a direction transverse to the coil axis 100. Pad 104 defines a similar surface and block (not shown). Pad 102 has a pair of electrical contacts 112 projecting from its surface. The coil unit may also include other components (not shown) commonly used in conjunction with a receiving coil as, for example, a tuning capacitor or a preamplifier, which may be disposed within one or both of the pads. Electrical connectors 112 are connected to the windings of the coil and to other electrical components. In use, these connectors are connected by a conventional cable (not shown) to the RF transmitting and/or receiving devices of the magnetic resonance apparatus. In other embodiments, connectors 112 can be replaced by a cable permanently connected to the coil.

The coil is engaged with the fixture-receiving unit 50 by positioning the coil as shown in FIG. 6 and advancing the coil downwardly towards the fixture-receiving unit, so that block 106 enters into the slot 64 in end riser 62 and the corresponding block on pad 104 enters into the slot 76 (FIG. 5) of end unit 60. As the blocks enter into the slots, they force the catches 66 and 77 (FIGS. 3 and 5) out of the slots against the bias of the spring arms. The catches have sloping surfaces facing towards the open ends of the slots for this purpose. When the coil is fully seated and the blocks are bottomed in the slots of the end units, the latch 66 within slot 64 engages in one of the slots 108 or 110 on block 106, and the corresponding latch 77 of end riser 60 engages the block on pad 104 in a similar fashion. Thus, the coil is firmly held in the end units. The toroidal housing 96 of the coil is received in the U-shaped cradle defined by the walls 88 and 90 of the fixture-receiving unit. In this condition, the coil axis 100 extends parallel to the cradle axis 92 and, hence, extends transverse to the track direction 40 of the mounting unit.

The coil is encompassed within the length of the fixture-receiving unit 50 in the track direction 40. That is, the coil is disposed between end risers 60 and 62. As pointed out above, the range of motion of the fixture-receiving unit relative to the mounting unit is limited so that the fixture-receiving unit remains entirely within the length of mounting unit 20 in the track direction. Therefore, the coil also will remain entirely within the length of the mounting unit 20.

Figure 7:
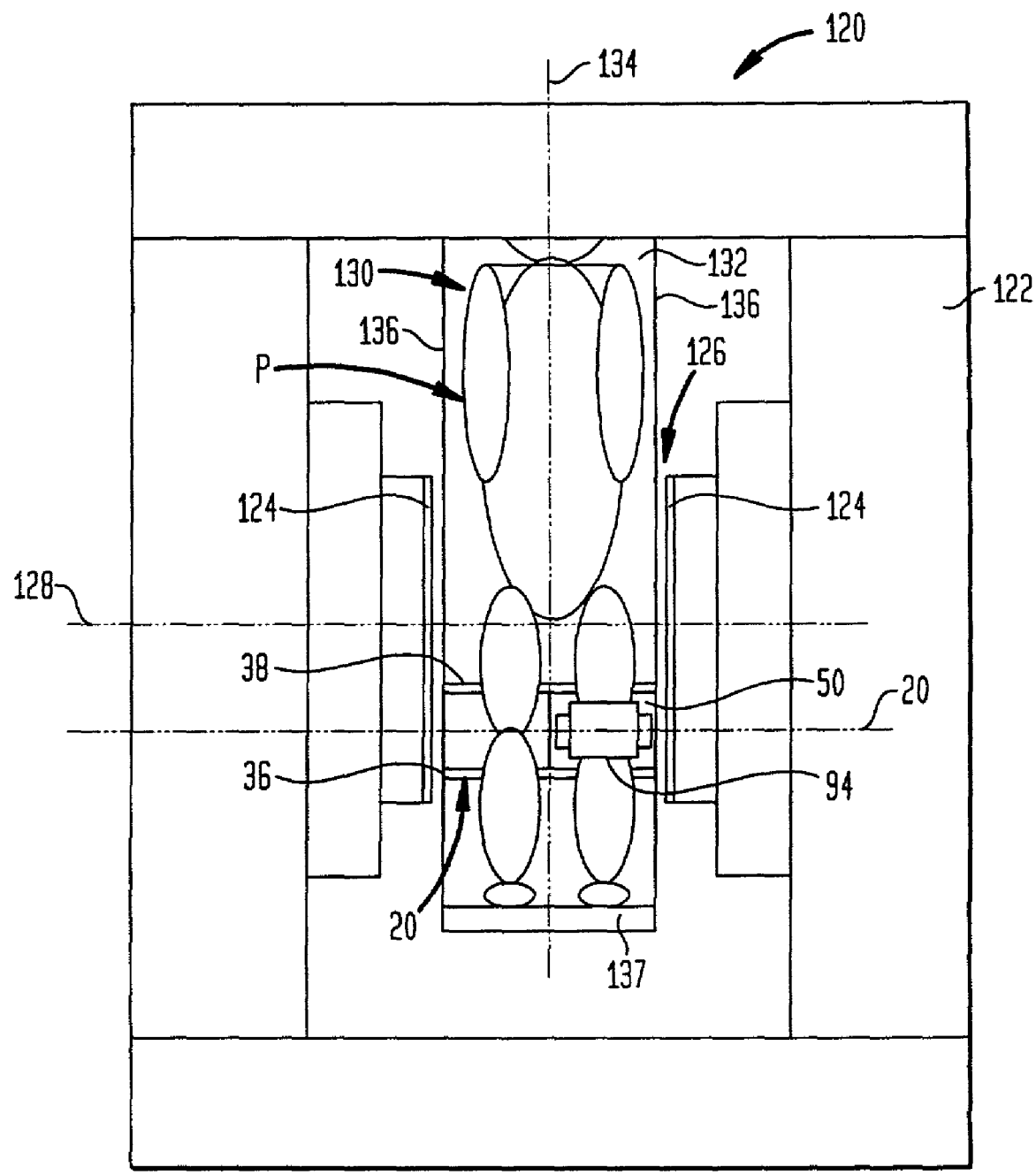
FIG. 7 is a diagrammatic elevational view of a magnetic resonance imaging system according to one embodiment of the invention incorporating the fixture-positioning apparatus of FIGS. 1-6.

The fixture-positioning apparatus is employed in conjunction with a magnetic resonance imaging apparatus 120 (FIG. 7). The particular apparatus illustrated is generally in accordance with the disclosure of the aforementioned copending, commonly assigned U.S. patent applications. It includes a magnet 122 which has a pair of opposed elements 124 defining a patient-receiving gap 126 between them. In the particular magnet illustrated, the opposed elements are pole faces, but in other types of magnets, these opposed elements may be elements of opposed superconducting or resistive electromagnet coils or other structures. The magnet is arranged to provide a magnetic field surrounding a magnet axis 128 within patient-receiving gap 126. The magnet axis extends substantially horizontally. The magnetic resonance imaging apparatus further includes a patient handling apparatus incorporating an elongated patient support 130 having a patient-receiving surface 132 and a longitudinal direction 134. A footrest 137 projects from surface 132 at one end. The patient-receiving surface is bounded by a pair of longitudinal edges 136. In the condition illustrated in FIGS. 7 and 8, the patient-receiving surface lies in a generally vertical plane and the longitudinal direction 134 of the patient support extends generally vertically, typically within about 15° of vertical. The widthwise or lateral dimension of the patient-receiving table transverse to longitudinal direction 134 is just slightly less than the dimension of gap 126 between opposed elements 124 of the magnet. The lateral dimension of the patient support is parallel to magnet axis 128.

Patient support 130 is associated with a carriage 138 and drive at 140 arranged to move the patient support 130 in its direction of elongation and to tilt the support between the vertical condition illustrated and a horizontal condition (not shown) in which the patient-receiving surface 132 and longitudinal direction 134 are generally horizontal.

Figure 9:
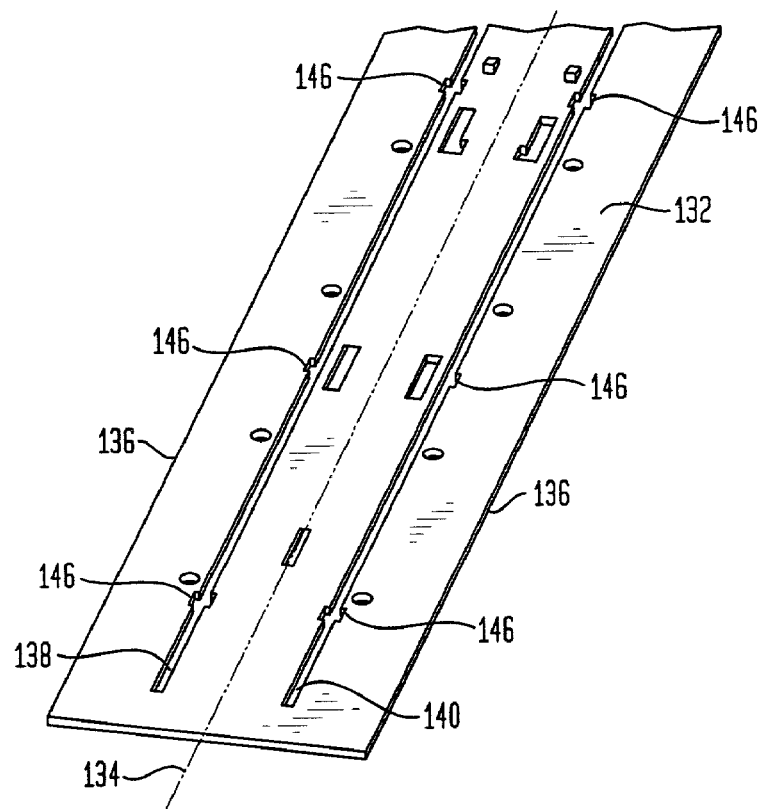
FIGS. 9 and 10 are fragmentary perspective views of a patient support incorporated in the apparatus of FIGS. 7 and 8.
Figure 10:
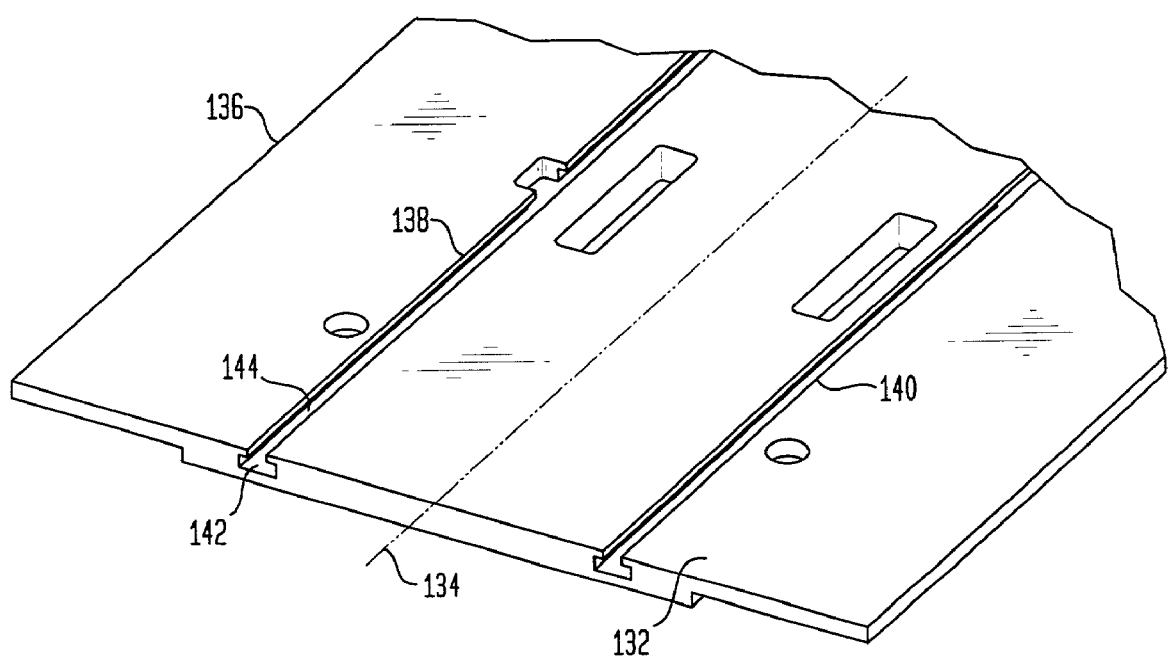

As seen in greater detail in FIGS. 9 and 10, the patient-receiving surface 132 has a pair of slots 138 and 140 extending parallel to one another and extending in the longitudinal direction 134 of the support. As best seen in FIG. 10, slots 138 and 140 are generally T-shaped in cross-section. Thus, each slot has a narrow top portion 144 where the slot opens to the surface 132 remote from the opening of the slot. Pockets 146 are provided in pairs (FIG. 9) along the lengths of the slots. These pockets are wider than the narrow portions 144 of the slots.

The fixture-positioning apparatus, with or without a fixture thereon, can be engaged with the patient support 130 of the MRI apparatus by placing the positioning apparatus against the patient-receiving surface 132 so that the bottom surface 24 of mounting unit 20 (FIG. 1) confronts surface 132, and so that one row of guides 26 is aligned with slot 138 and the other row of guides 28 is aligned with the slot 140. The center guides 26*b* and 28*b* are aligned with one set of pockets 146. In this condition, the heads 32 of the center guides (FIG. 1) enter into the pockets, whereas the end guides 26*a*, 26*c*, 28*a* and 28*c* are engaged in the narrow portions 144 of the slots. The apparatus is then shifted in the longitudinal direction of the table until it is at the desired location relative to the table. The heads 32 of the center guides are trapped in the wide portions 142 of the slots. Arresting catches 34 (FIG. 1) on the mounting unit frictionally engage the bottoms of slots 138 and 140 and, hence, hold the mounting unit in position along the length of the support. The mounting unit 20 desirably is installed on the patient support 130 so that the first rail 36 bearing the detent bumps 48 (FIG. 2) faces towards the footrest 137 at the foot end of the patient support. This assures that, when the patient support is in the vertical orientation as shown, gravity forces the fixture-positioning unit and fixture downwardly, towards the first rail and helps hold the detent bumps 48 in engagement with the detent notches 94 (FIG. 4) on the edge of the fixture-positioning unit base plate. Typically, the fixture-positioning apparatus is secured to the patient support before engaging the fixture with the fixture-positioning apparatus.

In the assembled condition, the mounting unit and, hence, the rest of the fixture-positioning assembly and the fixture are held firmly to the patient support. Also, in this condition, the mounting unit is constrained against movement relative to the table in the lateral direction, transverse to the longitudinal direction 134 of the patient support. The track direction 40 of the guide unit (FIGS. 2, 5 and 6) is transverse to the longitudinal direction of the table. The length of the guide unit in the track direction is less than or equal to the width of the patient support, i.e., slightly less than the distance between the longitudinal edges 136 of the patient support. Thus, the entire positioning assembly and fixture are contained within the width of the patient support. Fixture-positioning unit 50 and fixture 94 are also contained within the width of the patient support. As discussed above, the fixture-positioning unit and fixture can be moved in the track direction 20 over a limited range of motion. However, in any position of the fixture-positioning unit relative to the mounting unit, the fixture-positioning unit 50 and fixture 94 are entirely contained within the length of the mounting unit in the track direction 20 and, hence, entirely contained within the width of the patient support.

The technician can position the fixture readily, without the use of tools. The fixture can be repositioned as desired for a particular procedure. For example, as seen in FIG. 7, the fixture 94 is positioned to encompass the right knee of a patient P, and the patient's knee extends through the bore of the coil housing 94. The patient's left leg extends across mounting unit 20. However, because mounting unit 20 has a low profile and protrudes from the surface 132 of the patient support by only a small distance as, for example, about one inch, the mounting unit does not cause any substantial discomfort or impede positioning of the patient's left leg. Pillows or padding may be disposed between the patient and mounting unit 20.

Because the fixture or coil 94, and the entire fixture-positioning apparatus, including mounting unit 20 and fixture-positioning unit 50, are entirely disposed within the width of the patient support 130 between longitudinal edges 136, these components do not impede movement of the patient support 130. These components cannot collide with the gap-defining elements 124 of the magnet.

Figure 11:
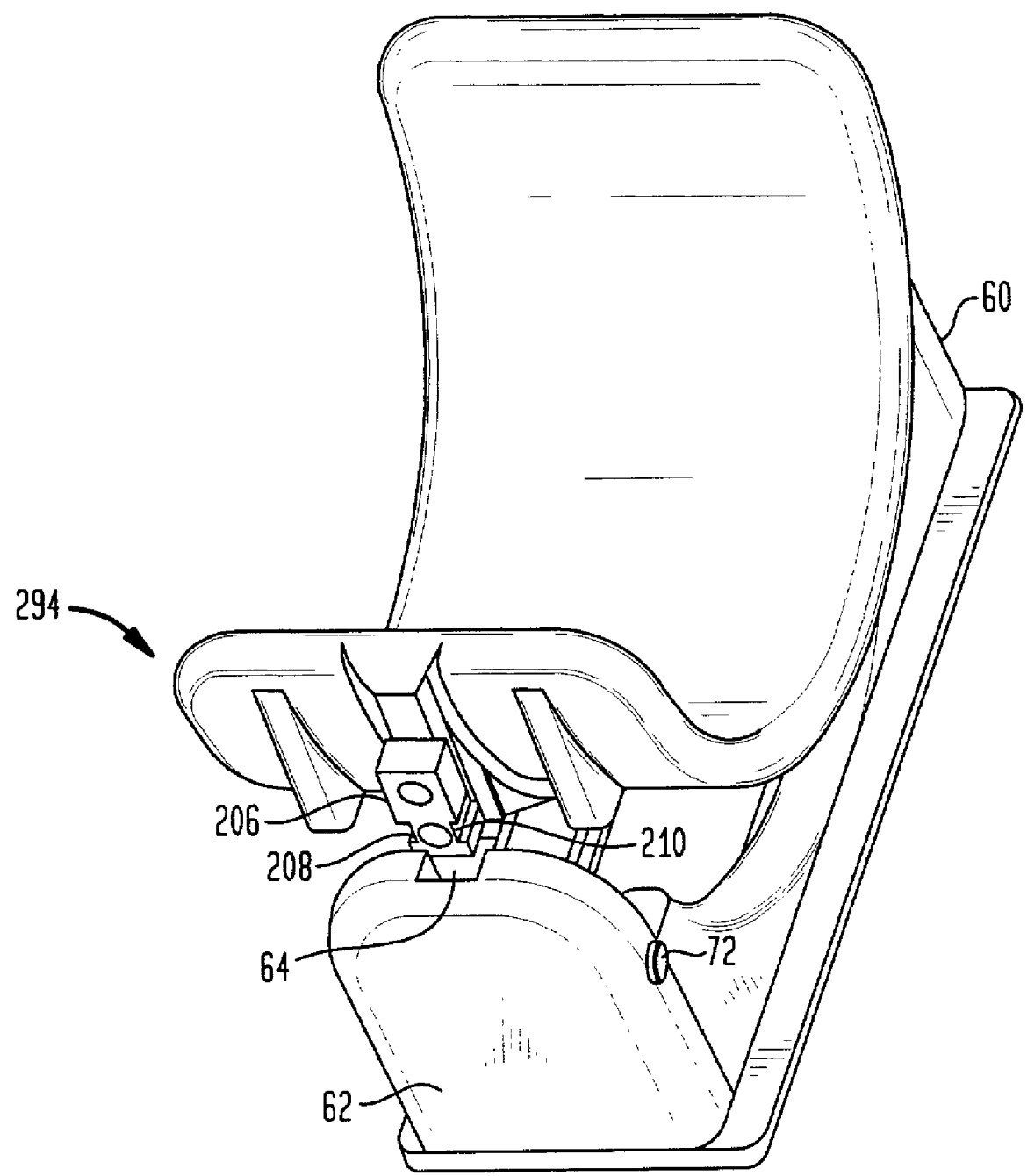
FIG. 11 is a diagrammatic perspective view depicting a part of the apparatus of FIGS. 1-5 in conjunction with a further fixture.

The same fixture-positioning apparatus, including mounting unit 20 and fixture-receiving unit 50, can be used to mount other fixtures. For example, as seen in FIG. 11, a generally U-shaped headrest 294 can be mounted in the fixture-positioning apparatus in place of coil 94. Headrest 294 is equipped with a block 206 identical to block 106 (FIG. 6) and with a corresponding block (not shown) on the opposite side of the headrest. The configuration of the blocks on the headrest is identical to the configuration of the blocks on coil 94. Thus, the headrest can be engaged in the mounting slot 64 of end unit 62 and in the corresponding mounting slot of end unit 60 in the same way as the coil 94. Still other fixtures can be provided with the same configuration of blocks, so that all of these fixtures can be used interchangeably. A fixture can be disengaged from the fixture-positioning assembly by depressing the release buttons 72 and 78 (FIGS. 3 and 6) to retract latches 66 and 77 out of engagement with the slots in the mounting blocks of the fixture and lifting the fixture out of the slots. This can be done while the fixture-positioning apparatus remains in place on the patient support.

The components of the fixture-positioning assembly desirably are formed from non-metallic materials as, for example, polymers such as acetal, commonly sold under the trademark Delrin, polyvinyl chloride, polycarbonate, commonly sold under the trademark Lexan, acrylic, commonly sold under the designation Plexiglass, or fiber-reinforced polymers such as that sold under the designation G10, or wood.

Figure 8:
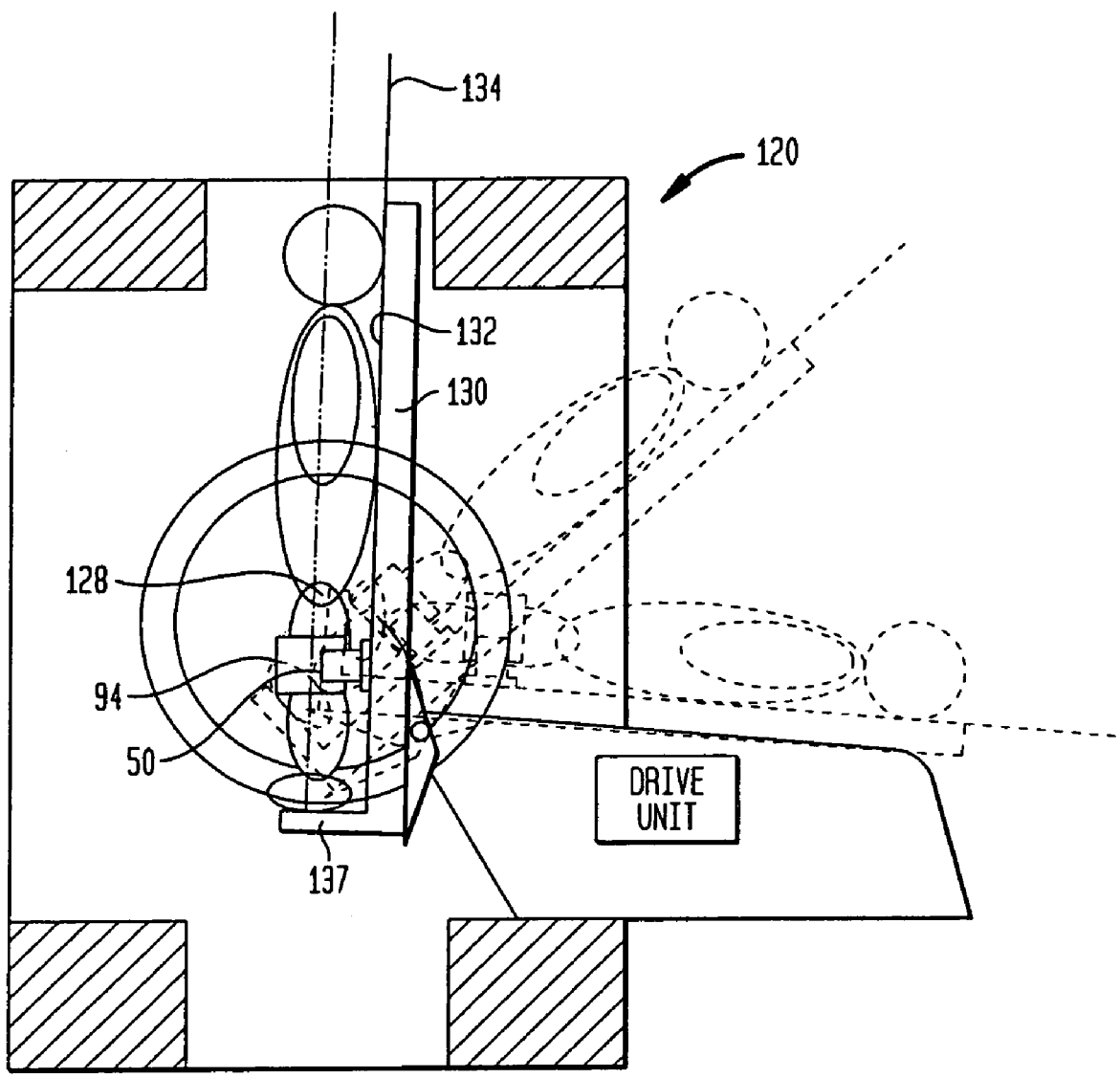
FIG. 8 is a diagrammatic sectional view of the apparatus shown in FIG. 7.

Numerous variations and combinations of the features discussed above can be utilized without departing from the present invention. For example, although only one fixture-positioning assembly is illustrated in FIGS. 7 and 8, the patient support can be equipped with as many fixture-positioning assemblies and fixtures as desired. Also, the frictional arresting elements 34 (FIG. 1) used to hold mounting unit 20 against movement in the longitudinal direction of the patient support can be replaced by other locking mechanisms. For example, the mounting unit can be provided with a manually operable cam, screw or other mechanism for forcibly engaging a locking element against the patient support. Alternatively, the patient support can be provided with a series of holes arranged in a row in the longitudinal direction of the support, and mounting unit 20 can be provided with a locking pin that can be selectively engaged in any one of these holes to hold the mounting unit in position. Also, other fastening devices such as bolts, hook and loop fasteners such as those sold under the trademark VELCRO, or suction cups can be employed. In a further variant, the patient support can be provided with an element adjustable in the longitudinal direction of the patient support, and the fixture positioning apparatus can be secured to this adjustable element. For example, the adjustable element may be a belt, chain or cable having a run extending in the longitudinal direction of the patient support, and the patient support may include an appropriate mechanism such as a set of drums or sprockets for controllably moving the belt, chain or cable. In this arrangement, the position of the fixture positioning apparatus in the longitudinal direction of the patient support can be adjusted by moving the adjustable element.

As discussed above, gravity tends to hold the detent bumps 48 (FIG. 2) in engagement with the detent notches 94 (FIG. 4) while the assembly is mounted on the patient support which is in a vertical orientation. To assure that the bumps and notches remain engaged when the patient support is tilted to a horizontal orientation, a spring (not shown) may be provided on the second rail 38 or on the edge 54 of base plate 52 so as to urge the base plate towards the first rail 36 and detent bumps 48. Other types of detent mechanisms can be substituted for the bumps and notches discussed above. For example, the track can be dimensioned so as to prevent movement of the base plate transverse to the track direction. One or more spring-loaded detent elements can be mounted on first rail 36 so that these elements engage in detent notches 94. Alternatively, the mounting unit 20 can be provided with a series of holes arranged in a row along the track direction 40 and the fixture-receiving unit 50 can be provided with a manually operable locking pin, which can be engaged in any of these holes. The configuration of the track on the mounting unit can be varied. For example, the mounting unit can have a track element of square, dovetail or other configuration projecting upwardly from the surface of bottom plate 22, and the fixture-receiving unit 50 can be provided with a slot engagable on this track element.

In a further variant, the detent arrangement may be omitted entirely and an appropriate brake or grasp mechanism may be provided on the fixture-positioning unit or on the mounting unit for locking the fixture-receiving unit to the mounting unit at any position along the track. Also, a screw may be provided on one unit and engaged with the mating unit so that the position of the fixture-receiving unit in the track direction can be adjusted by turning the screw. In all of these variants, it is desirable to provide stops to limit the range of motion of the fixture-receiving unit relative to the mounting unit as described above.

The elements which mount the fixture to the fixture-receiving unit, such as the blocks 106 (FIG. 6) and the mating slots 64 on the fixture-receiving unit, can be replaced by other types of inter-engagable elements. For example, the fixtures can be provided with pins and the fixture-receiving unit can have mating holes, or vice-versa. Here again, however, the mating elements on each fixture should be identical to those on other fixtures, so that the fixtures can be used interchangeably. The mounting unit or the fixture-receiving unit can be configured to provide additional degrees of freedom in positioning of the fixture relative to the patient support. For example, the end risers 62 and 60 of the fixture-receiving unit can be arranged to tilt relative to the base plate 54 and, thus, allow the fixture to tilt relative to the patient-receiving table. Also, the end risers may be provided with mechanisms for elevating the fixture away from the base plate 54 or lowering the fixture toward the base plate.

In the embodiments discussed above with reference to FIGS. 1-10, the fixture-receiving unit is arranged to hold a coil so that the coil axis extends perpendicular to the track axis and thus extends parallel to the longitudinal direction 134 of the patient support. However, the apparatus can be arranged to hold a coil in other orientations as, for example, at angles oblique to the longitudinal direction of the patient support. Desirable orientations for coils are discussed in greater detail in copending, commonly assigned U.S. Provisional Patent Application No. 60/327,329, filed Oct. 5, 2001, the disclosure of which is hereby incorporated by reference herein.

A system in accordance with a further embodiment of the invention includes a patient support 230 in the form of an elongated table having a patient-receiving surface 232, lateral edges 236 and a direction of elongation 234 similar to the corresponding features of the patient support 130 discussed above with reference to FIGS. 8-10. In this embodiment, the fixture-positioning apparatus includes a large number of support attachment elements 202 in the form of holes extending into patient support 230 from the patient support surface 232. Support attachment elements or holes 202 are arranged in a rectilinear array with rows extending in the lateral direction, transverse to direction of elongation 234, and with columns extending in the longitudinal direction 234. The holes in the outermost columns of the array, closest to lateral edges 236 define an edge distance $D_E$ from the center of the holes in such columns to the adjacent edge 236 of the support. The holes 202 in each row are disposed at the same center-to-center distance or pitch $D_R$, which is uniform throughout the array. Also, the adjacent holes in each column are disposed at a pitch $D_C$, which is also uniform throughout the array, but which may or may not be equal to $D_R$.

Figure 12:
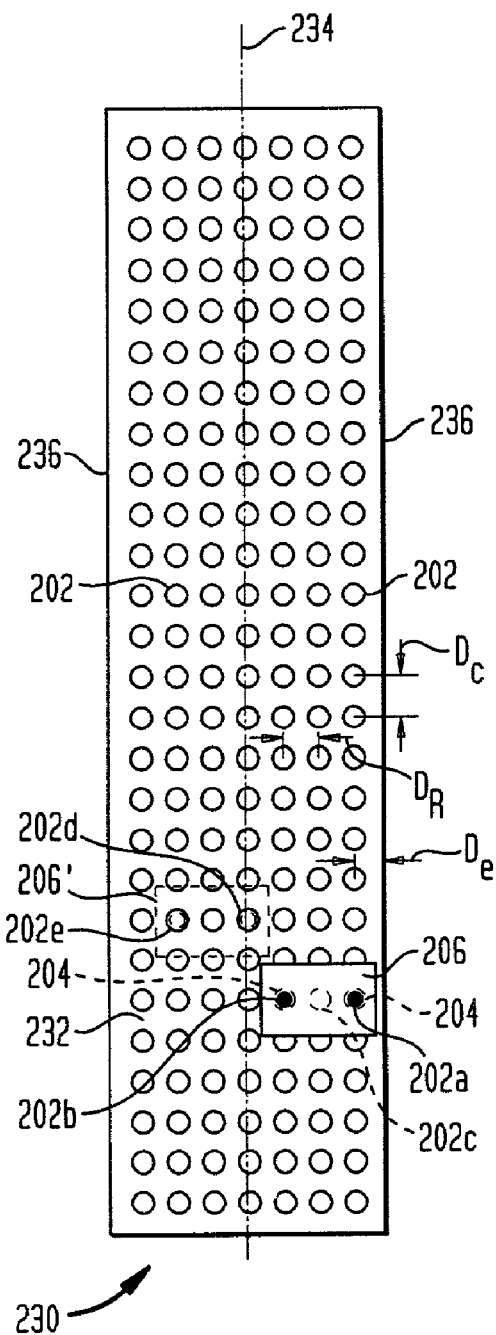
FIG. 12 is a diagrammatic plan view of a patient support incorporated in apparatus according to a further embodiment of the invention.
Figure 13:
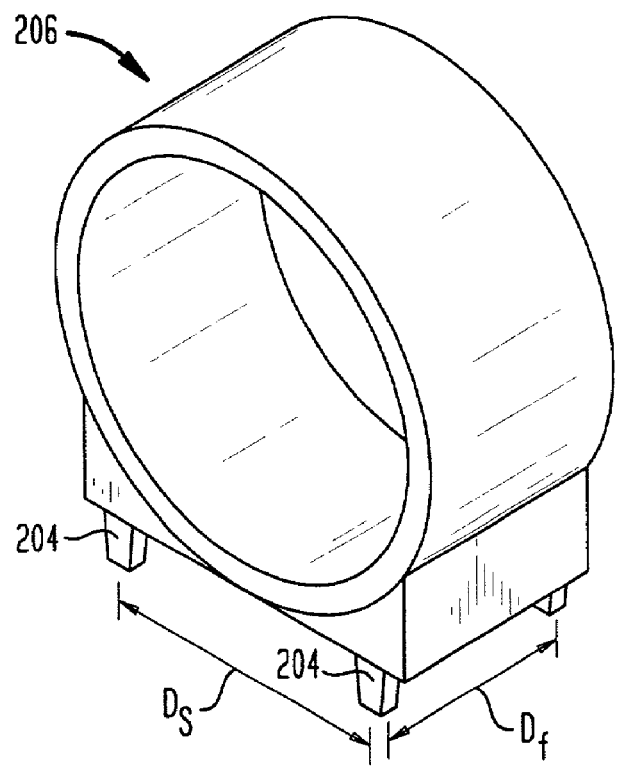
FIG. 13 is a diagrammatic perspective view of a fixture and associated components used with the patient support of FIG. 12.

The fixture-positioning apparatus also includes fixture attachment elements 204 (FIG. 13) mounted on a first fixture 206 to be used with the patient support. Thus, a first fixture 206 has a pair of fixture attachment elements 204 at a first spacing $D_S$ from one another. The spacing $D_S$ between the two pins 204 on the first fixture 206 is equal to an integral multiple of $D_R$, in this case twice $D_R$. Also, the distance $D_F$ from each pin 204 to the adjacent edge of the first fixture 206 is less than $D_E$. Thus, as shown in FIG. 12, the fixture attachment elements or pins 204 of the first fixture may be engaged with a set of support attachment elements or holes 202, including holes 202a and 202b, so as position the first fixture 206 at the location indicated in FIG. 12 in solid lines. Holes 202a and 202b constitute a first set of support attachment elements. The holes 202a and 202b constituting the first set of support elements are spaced apart from one another by twice $D_R$, i.e., an additional hole 202c is disposed between the holes 202a and 202b of this set.

Every other set of holes 202 spaced apart from one another by twice $D_R$ constitutes another set of support attachment elements which can receive the fixture attachment elements 204 on the first fixture 206. Thus, fixture 206 can be positioned at any one of many locations by engaging the fixture attachment elements or pins 204 on the first fixture with any similar set of support attachment elements or holes 202. For example, first fixture 206 can be positioned at position 206' shown in broken lines in FIG. 12 by engaging pins 204 with a set of holes 202d and 202e. However, because the distance $D_F$ from each pin 204 to the edge of fixture 206 is less than the edge distance $D_E$ from any hole 202 in the outermost row to the longitudinal edge 236 of the patient support, the first fixture 206 will always be disposed entirely between the longitudinal edges 236 of the patient support. As discussed above, this assures that the first fixture will not interfere with the gap-defining elements of the MRI apparatus during movement of the patient support.

Figure 14:
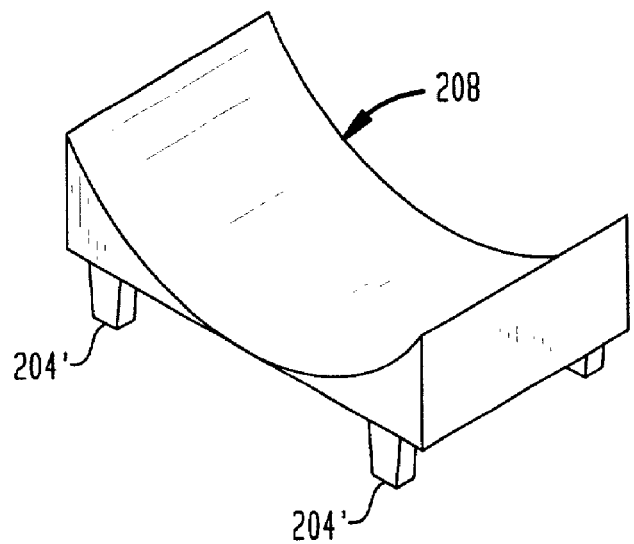
FIG. 14 is a diagrammatic perspective view of another fixture usable with the patient support of FIG. 12.

The system desirably includes one or more additional fixtures, such as a second fixture 208 (FIG. 14). The second fixture 208 has fixture attachment elements or pins 204' arranged in substantially the same way as the fixture attachment elements 204 of the first fixture, so that the second fixture can be engaged with a set of holes or support attachment elements to mount the second fixture to the patient support in addition to, or in lieu of, the first fixture. In a further variant, the spacing between the fixture attachment elements 204' of the second fixture can be different from the spacing between the fixture attachment elements of the first fixture, provided that this different spacing is an integral multiple of the row distance $D_R$ or the column distance $D_C$. For example, a relatively small fixture can be provided with pins 204' at a distance equal to $1 \times D_R$ or $1 \times D_C$. In a further variant, a very small fixture may have only one pin mountable in a set of support attachment elements consisting of only one hole 202.

The pins 204 are arranged to engage securely in holes 202. In the particular embodiment illustrated, the pins 204 are tapered, and each hole 204 has a mating taper. This arrangement may be similar to the common Morse taper fittings used in machine shop practice. In other variants, pins 204 can be provided with threads, and holes 202 may have mating threads. In yet another variant, the pins may be equipped with expansible elements or latches that can be engaged with mating fixtures around each hole 204. Essentially, any arrangement of mutually engagable parts which provides a secure attachment can be employed. In an alterantive arrangement, the engageable elements can include strips of a hook and loop fastener on the fixture and on the patient support, these being arranged so that the range of fixture positions relative to the support is limited.

In yet another variant, the support can define a multiplicity of tracks similar to the track 46 defined by the mounting unit discussed above with reference to FIG. 2, and the fixture may have a foot similar to the base 52 of the fixture-positioning unit discussed above with reference to FIGS. 3 and 4. Desirably, these tracks extend in the lateral direction of the support and are disposed at spaced-apart locations along the length of the support.

Figure 3:
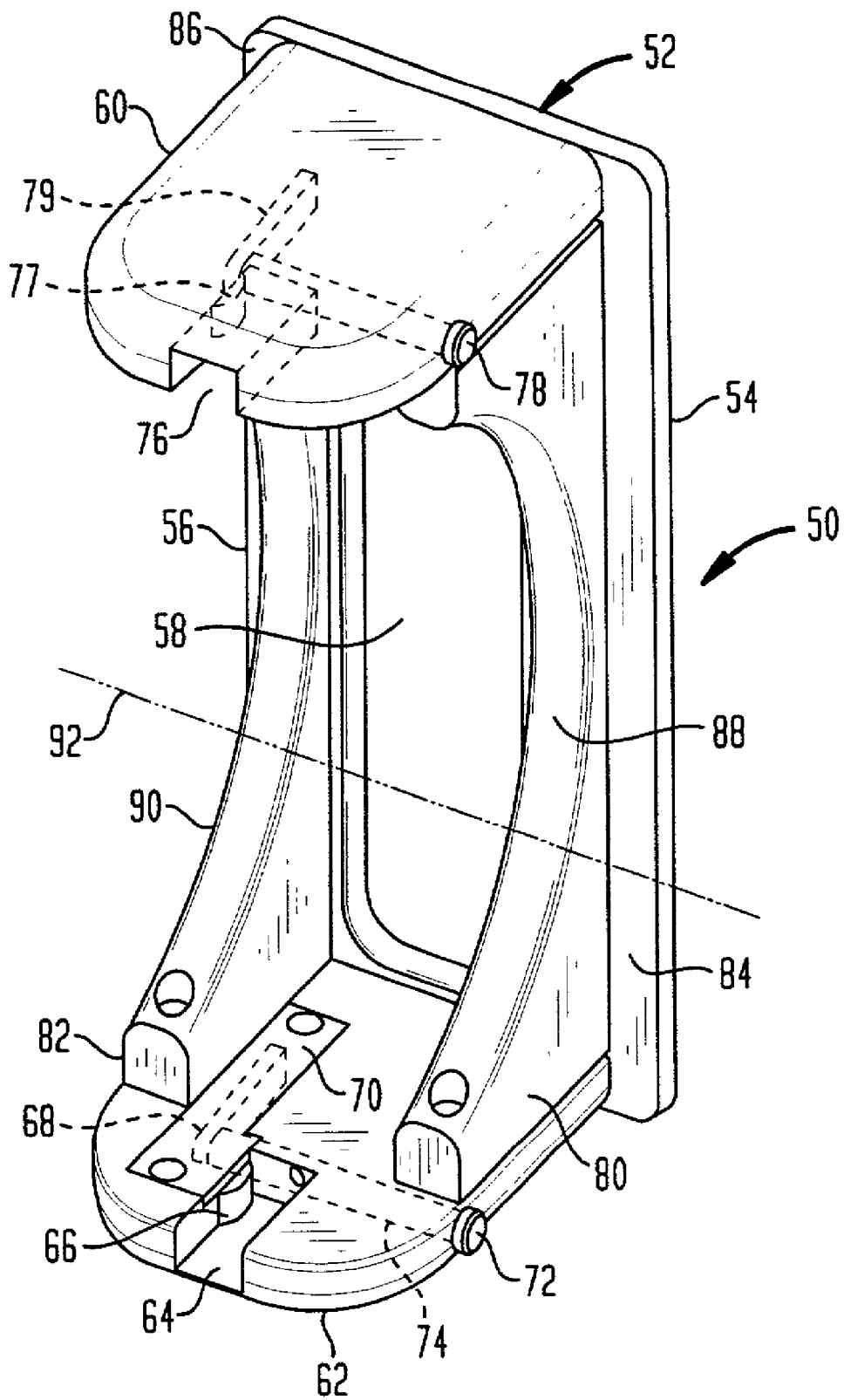
FIG. 3 is a diagrammatic perspective view of another component usable with the component of FIG. 1.

In a still further variant, a fixture-positioning unit as discussed with reference to FIGS. 3 and 4 can be used with a patient support defining multiple tracks.

As these and other variations and combinations can be employed, the foregoing description of the preferred embodiments should be taken by way of illustration rather than by way of limitation of the invention as defined by the claims.

The invention claimed is:

1. A magnetic resonance imaging system comprising:
a magnetic resonance imager;
magnetic resonance apparatus having a structure including opposed elements defining a patient-receiving gap therebetween and arranged to provide a magnetic field in the gap along a horizontal field axis;
a patient support having a top surface for supporting a patient's body and a bottom surface, said patient support movable relative to said structure through a range of support positions, the patient support including a pair of longitudinal edges extending between said top and bottom surfaces in a longitudinal direction transverse to the horizontal field axis so as to define a patient support surface that includes a lateral dimension less than the dimension of the gap and parallel to the horizontal field axis, the patient support further including one or more continuous tracks on said top surface and extending along the patient support parallel to the longitudinal direction, said one or more continuous tracks being positioned entirely between said longitudinal edges;

a fixture-positioning apparatus constructed and arranged to move within said one or more continuous tracks; and a fixture usable in conjunction with said magnetic resonance apparatus, said fixture-positioning apparatus being operative to secure the fixture to the patient support and to permit adjustment of the position of the fixture relative to the patient support over a range of fixture positions, said range of fixture positions being limited so that for any position of said fixture within said range of fixture positions, said fixture will remain clear of said opposed elements during movement of said patient support through said range of support positions, wherein said range of support positions includes a range of movement in the longitudinal direction of said patient support, and wherein said range of fixture positions includes a lateral range of positions in a lateral direction transverse to the longitudinal direction.

2. A system as claimed in claim 1 wherein said range of positions in said lateral direction is limited so that for any position in said lateral range, said fixture is disposed entirely between said longitudinal edges of said patient support.

3. A system as claimed in claim 1 wherein said fixture-positioning apparatus includes a mounting unit, one or more mount attachments connecting said mounting unit to said patient support, and a fixture-positioning unit engaged with said fixture, said fixture-positioning unit being adjustable relative to said mounting unit in said lateral direction.

4. A system as claimed in claim 3 wherein said patient support includes one or more support tracks extending in the longitudinal direction of the support and said one or more mount attachments include one or more guide elements arranged to engage said one or more support tracks so that the mounting unit can be adjusted relative to the support in said longitudinal direction.

5. A system as claimed in claim 3 wherein said fixture is a coil having an axis extending in said longitudinal direction.

6. A system as claimed in claim 3 wherein said fixture-positioning apparatus includes a releasable connection releasably holding said fixture to said fixture-positioning unit so that said fixture can be removed.

7. A system as claimed in claim 6 further comprising one or more additional fixtures, said releasable connection being arranged to engage said one or more additional fixtures when said fixture is removed from said releasable connection.

8. A system as claimed in claim 1 wherein said fixture-positioning apparatus includes one or more fixture attachment elements mechanically connected to said fixture and a plurality of support attachment elements on said patient support, said fixture attachment elements being engagable with a plurality of different sets of said support attachment elements.

9. A system as claimed in claim 8 wherein said fixture attachment elements and said support attachment elements are constructed and arranged so that when said fixture engagement elements are engaged with any set of said support attachment elements, said fixture is disposed entirely between said longitudinal edges of said patient support.

10. A system as claimed in claim 8 wherein said support attachment elements are arranged in an array extending in said longitudinal direction and said lateral direction.

11. A system as claimed in claim 10 wherein said support attachment elements include holes in said patient support.

12. Apparatus for positioning a fixture in a magnetic resonance apparatus comprising:

a mounting unit;

an elongated patient support having a top surface for supporting a patient's body, a bottom surface, a pair of longitudinal edges extending in a direction of elongation, and a pair of continuous tracks extending along the top surface of said patient support in the elongation direction, said pair of tracks being positioned entirely between said pair of longitudinal edges of said patient support, said patient support being capable of moving through a range of support motions and said continuous tracks being capable of moving through said range of support motions while said elongated patient support is moving through said range of support motions;

one or more mount attachments joined to the mounting unit, the one or more mount attachments being adapted to connect said mounting unit to the continuous tracks on the patient support of the magnetic resonance apparatus, the mount attachments being adapted to translate in the continuous tracks in the elongation direction; and a fixture-receiving unit, said fixture-receiving unit being adapted to hold said fixture, said fixture-receiving unit and said mounting unit being engagable with one another so that said fixture-receiving unit can be adjusted over a range of positions relative to said mounting unit, whereby a fixture held in said fixture-receiving unit can be adjusted in position relative to the patient support of the magnetic resonance apparatus.

13. Apparatus as claimed in claim 12 wherein said one or more mount attachments are arranged to hold said mounting unit to the elongated patient support so that said mounting unit is in a predetermined position relative to the longitudinal edges of the patient support and wherein said fixture-receiving unit and said mounting unit cooperatively limit said range of positions relative to said longitudinal edges.

14. Apparatus as claimed in claim 13 wherein said range of positions encompasses only positions in which said fixture-receiving unit is disposed entirely between said longitudinal edges.

15. Apparatus as claimed in claim 13 wherein said mounting unit defines a track direction, said mount attachments are arranged to secure the mounting unit to the patient support so that said track direction is transverse to the direction of elongation of the table, and said fixture-receiving unit is movable in said track direction relative to said mounting unit when said fixture-receiving unit is engaged with said mounting unit.

16. Apparatus as claimed in claim 15 wherein said fixture-receiving unit and said mounting unit have stops engagable with one another to limit the position of said fixture receiving-unit in said track direction.

17. Apparatus as claimed in claim 15 wherein said fixture-receiving unit is adapted to hold a coil in a pre-determined position, wherein the coil has an axis and wherein the pre-determined position is one wherein the axis of the coil extends transverse to the track direction.

18. Apparatus as claimed in claim 16 wherein said fixture-receiving unit includes semi-circular panels that define a cradle, the cradle having an axis disposed transverse to the track direction.

19. Apparatus as claimed in claim 15 further comprising detents arranged to hold said fixture-receiving unit at predetermined locations along said track direction.

20. A method of operating a patient support of a magnetic resonance system said patient support including a top surface for supporting a patient's body, a bottom surface, and a first and second pair of opposed edges extending between said top and bottom surfaces, said method comprising the steps of:
   (a) positioning a fixture on said patient support of said magnetic resonance apparatus using a fixture-positioning apparatus;
   (b) slidably adjusting the fixture relative to the patient support;
   (c) moving the patient support within a range of support positions between a pair of magnet elements defining a gap including tilting the patient support between an upright and horizontal position, the pair of magnet elements being operable to generate a static magnetic field along a horizontal field axis and wherein the top surface of the patient support lies in a plane parallel to the horizontal field axis, the fixture-positioning apparatus limiting the position of the fixture after said adjusting step so that the fixture does not interfere with the pair of magnet elements during said moving step; and
   (d) disengaging the fixture from the fixture-positioning apparatus, replacing the fixture with another fixture, and repeating said positioning and moving steps.

21. A method as claimed in claim 20 further comprising the step of placing a patient on the patient support.

22. A method as claimed in claim 20 wherein said step of positioning the fixture includes adjusting the position of the fixture relative to the patient support by adjusting the fixture-positioning apparatus.

23. A method as claimed in claim 20 wherein said step of positioning the fixture includes engaging positioning elements on the fixture with mating features on the patient support.

* * * * *